(12) United States Patent
Bakken et al.

(10) Patent No.: US 11,911,587 B2
(45) Date of Patent: Feb. 27, 2024

(54) INJECTION SETUP KITS AND METHODS

(71) Applicant: ACIST Medical Systems, Inc., Eden Prairie, MN (US)

(72) Inventors: Matthew James Russell Bakken, Bloomington, MN (US); Spencer Fodness-Bondhus, Columbia Heights, MN (US); Blaise D. Porter, Minneapolis, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 772 days.

(21) Appl. No.: 17/006,973

(22) Filed: Aug. 31, 2020

(65) Prior Publication Data

US 2022/0062530 A1 Mar. 3, 2022

(51) Int. Cl.
*A61M 5/00* (2006.01)
*A61B 6/00* (2006.01)
(Continued)

(52) U.S. Cl.
CPC ............. *A61M 5/002* (2013.01); *A61B 6/481* (2013.01); *A61B 10/0045* (2013.01);
(Continued)

(58) Field of Classification Search
CPC ...... A61M 5/002; A61M 5/007; A61M 5/365; A61M 39/10; A61M 2005/1403;
(Continued)

(56) References Cited

U.S. PATENT DOCUMENTS 4,252,131 A 2/1981 Hon et al.
4,714,461 A 12/1987 Gabel
(Continued)

FOREIGN PATENT DOCUMENTS

WO 2006060688 A2 6/2006
WO 2014047626 A2 3/2014
WO 2015126526 A1 8/2015

OTHER PUBLICATIONS

International Search Report and Written Opinion dated Dec. 14, 2020 for related International Application No. PCT/US2021/047064, 16 pgs.
(Continued)

*Primary Examiner* — Keith M Raymond
*Assistant Examiner* — Patrick M Mehl
(74) *Attorney, Agent, or Firm* — Crowell & Moring LLP

(57) ABSTRACT

An injection setup kit can include a manifold connector, a first packaging container, and a fluid line. The first packaging container can define a first closed interior volume that includes a patient interface connector having a patient interface inlet, a first patient interface outlet, and a valve configured to selectively permit fluid communication through the patient interface connector. The patient interface inlet can be fluidly connected to the manifold outlet. The fluid line can have a first fluid line end and a second fluid line end. The first fluid line end can be connected to the patient interface inlet within the first closed interior volume. The second fluid line end can extend outside of the first closed interior volume and be connected to a manifold outlet outside of the first closed interior volume.

12 Claims, 7 Drawing Sheets

(51) Int. Cl.
  *A61B 10/00* (2006.01)
  *A61M 5/36* (2006.01)
  *A61M 39/10* (2006.01)
  *A61M 5/14* (2006.01)
  *A61M 5/31* (2006.01)
(52) U.S. Cl.
  CPC ............ *A61M 5/007* (2013.01); *A61M 5/365* (2013.01); *A61M 39/10* (2013.01); *A61M 2005/1403* (2013.01); *A61M 2005/3128* (2013.01); *A61M 2205/502* (2013.01)
(58) Field of Classification Search
  CPC .... A61M 2005/3128; A61M 2205/502; A61M 2209/06; A61B 6/481; A61B 10/0045
  See application file for complete search history.

(56) References Cited

U.S. PATENT DOCUMENTS

| | | | |
|---|---|---|---|
| 4,759,751 | A | 7/1988 | Gabel et al. |
| 5,002,059 | A | 3/1991 | Crowley et al. |
| 5,334,153 | A | 8/1994 | McIntyre et al. |
| 5,421,334 | A | 6/1995 | Jabba |
| 5,695,468 | A | 12/1997 | Lafontaine et al. |
| 5,800,383 | A | 9/1998 | Chandler et al. |
| 7,037,271 | B2 | 5/2006 | Crowley |
| 8,758,294 | B2 | 6/2014 | Kim et al. |
| 2002/0111645 | A1 | 8/2002 | Wang et al. |
| 2004/0230213 | A1 | 11/2004 | Wulfman et al. |
| 2006/0118472 | A1 | 6/2006 | Schick et al. |
| 2008/0086087 | A1* | 4/2008 | Spohn ................ A61M 5/1408 604/151 |
| 2008/0287798 | A1 | 11/2008 | Lee et al. |
| 2009/0312740 | A1 | 12/2009 | Kim et al. |
| 2011/0237955 | A1 | 9/2011 | Dietz et al. |
| 2014/0257105 | A1 | 9/2014 | Dausch et al. |
| 2015/0209515 | A1* | 7/2015 | Houde .................... A61M 5/19 600/432 |
| 2016/0324503 | A1 | 11/2016 | Norris et al. |
| 2017/0049955 | A1* | 2/2017 | Uber, III ............. A61M 5/1408 |
| 2017/0312543 | A1* | 11/2017 | Franci .................. A61M 5/002 |
| 2018/0318495 | A1* | 11/2018 | Brady ............... A61M 5/16813 |

OTHER PUBLICATIONS

Shipping and Handling of Dangerous Goods—Table 1, published by SPNHC on Jul. 7, 2016 and retrieved from URL https://web.archive.org/web/07072016014428/https://spnhc.biowikifam.net/wiki/Shipping_and_Handling_of_Dangerous_Goods on Jan. 10, 2020. (Year:2016).
Ethyl Alcohol (Ethanol) Grade Selector, published online on Jul. 13, 2014 by Spectrum Chemical and retrieved from URL https://web.archive.org/web/20140713043431/https://www.spectrumchemical.com/OA_HTML/Ethyl-Alcohol-Grade-Selector.jsp?minisite=10020&respid=22372 on Jan. 10, 2019 (Year: 2014).

* cited by examiner

INJECTION SETUP KITS AND METHODS

TECHNICAL FIELD

This disclosure generally relates to the field of medical technology and, more particularly, to kits and methods for an injection system.

BACKGROUND

Injection systems can be used in a variety of medical applications. For example, injection systems can be used to introduce fluid into a patient to facilitate medical diagnostic and/or interventional procedures. In some such procedures, this fluid can assist in the collection of information, such as image data, at a region of interest within the patient. This collected information can be used to ascertain characteristics relevant to the diagnostic procedure and/or guide the placement of one or more medical devices during the interventional procedure.

However, significant time and attention can be required to properly set up an injection system. Setting up an injection system can require a number of component connections. For example, certain injection system components are intended for a limited number of uses (e.g., single-use) and need to be replaced frequently. In addition, in some cases, once the component connections are made, setting up an injection system can require that certain actions be performed before fluid can be introduced into a patient. One such action can be an air purge, in which fluid is conveyed through the connected injection system components to remove any air entrained in these components. In some instances, in order to maintain the sterility of certain components, some setup actions are taken by a non-sterile user while other setup actions are taken by a sterile user. Thus, significant time and attention can be required on the part of multiple users to properly set up an injection system.

SUMMARY

In general, various embodiments relating to injection setup kits and methods are disclosed herein. Various such embodiments can be useful, for instance, in facilitating more efficient workflow in preparing a fluid injection system for use. Embodiments disclosed herein can allow certain fluid injection system components to be set up in advance of an application in which the fluid injector is needed while preserving the sterility of particular components. Notably, embodiments disclosed herein can allow the advance setup of certain components while the procedural environment is relatively calm since this setup can occur prior to an emergency situation where time pressures would be present. Then, when the need to use the fluid injection system later arises, the time and attention needed to bring the injection system to a usable state is greatly reduced. This can be particularly valuable in fluid injection applications where time is of the essence. For instance, in certain applications, a matter of seconds can be the difference between a successful procedure and irreversible anatomic trauma (e.g., irreversible cardiac muscle trauma). Embodiments disclosed herein can, therefore, increase the likelihood of a successful procedure by reducing the time it takes to prepare an injection system for use in the procedure.

One embodiment includes an injection setup kit. This injection setup kit embodiment includes a manifold connector, a first packaging container, and a fluid line. The manifold connector includes a first manifold inlet and a manifold outlet. The first packaging container defines a first closed interior volume. This first closed interior volume can include a patient interface connector having a patient interface inlet, a first patient interface outlet, and a valve that is configured to selectively permit fluid to be communicated through the patient interface connector from the patient interface inlet to the first patient interface outlet. The patient interface inlet can be fluidly connected to the manifold outlet. The fluid line can have a first fluid line end and a second fluid line end. The first fluid line end can be connected to the patient interface inlet within the first closed interior volume of the first packaging container. The second fluid line end can extend outside of the first closed interior volume of the first packaging container and be connected to the manifold outlet outside of the first closed interior volume of the first packaging container.

A further embodiment of the injection setup kit includes a second packaging container separate from the first packaging container. In this embodiment, the second packaging container defines a second closed interior volume. This second closed interior volume can include the manifold connector. The second fluid line end can extend outside of the first closed interior volume of the first packaging container and extend into the second closed interior volume of the second packaging container such that the second fluid line end is connected to the manifold outlet within the second closed interior volume of the second packaging container.

Another embodiment includes a method of setting up an injection system. This method embodiment includes opening a first packaging container and removing from the first packaging container a manifold connector. The manifold connector removed from the first packaging container can include a first manifold inlet and a manifold outlet. The manifold outlet of the manifold connector removed from the first packaging container can be connected to one end of a fluid line, and another end of the fluid line can extend within a closed interior volume of a second packaging container. After opening the first packaging container, this method embodiment includes fluidly connecting the first manifold inlet to a contrast fluid reservoir. The contrast fluid reservoir can define a first internal reservoir volume that includes a first plunger. After connecting the first manifold inlet to the contrast fluid reservoir, this method embodiment includes delivering contrast fluid from the contrast fluid reservoir along the fluid line to a fluid collection receptacle that is within the closed interior volume of the second packaging container. After delivering contrast fluid to the fluid collection receptacle, this method embodiment includes opening the second packaging container and removing from the second packaging container the another end of the fluid line, the fluid collection receptacle, and a patient interface connector that is in fluid communication with the fluid line. And, after opening the second packaging container, this method embodiment includes fluidly connecting the patient interface connector to an injection catheter.

The details of one or more examples are set forth in the accompanying drawings and the description below. Other features, objects, and advantages will be apparent from the description and drawings.

BRIEF DESCRIPTION OF THE DRAWINGS

The following drawings are illustrative of particular embodiments of the present invention and therefore do not limit the scope of the invention. The drawings are intended for use in conjunction with the explanations in the following description. Embodiments of the invention will hereinafter be described in conjunction with the appended drawings, wherein like numerals denote like elements.

FIG. 3 shows components, previously enclosed in the second packaging container, connected to corresponding components of an injection system.

FIG. 4 shows components, previously enclosed in the second packaging container, connected to corresponding components of an injection system. FIG. 4 also shows certain components, previously enclosed in the first packaging container, connected to an injection catheter.

DETAILED DESCRIPTION

The following detailed description is exemplary in nature and is not intended to limit the scope, applicability, or configuration of the invention in any way. Rather, the following description provides some practical illustrations for implementing embodiments of the present invention. Examples of constructions, materials, and/or dimensions are provided for selected elements. Those skilled in the art will recognize that many of the noted examples have a variety of suitable alternatives.

Figure 1:
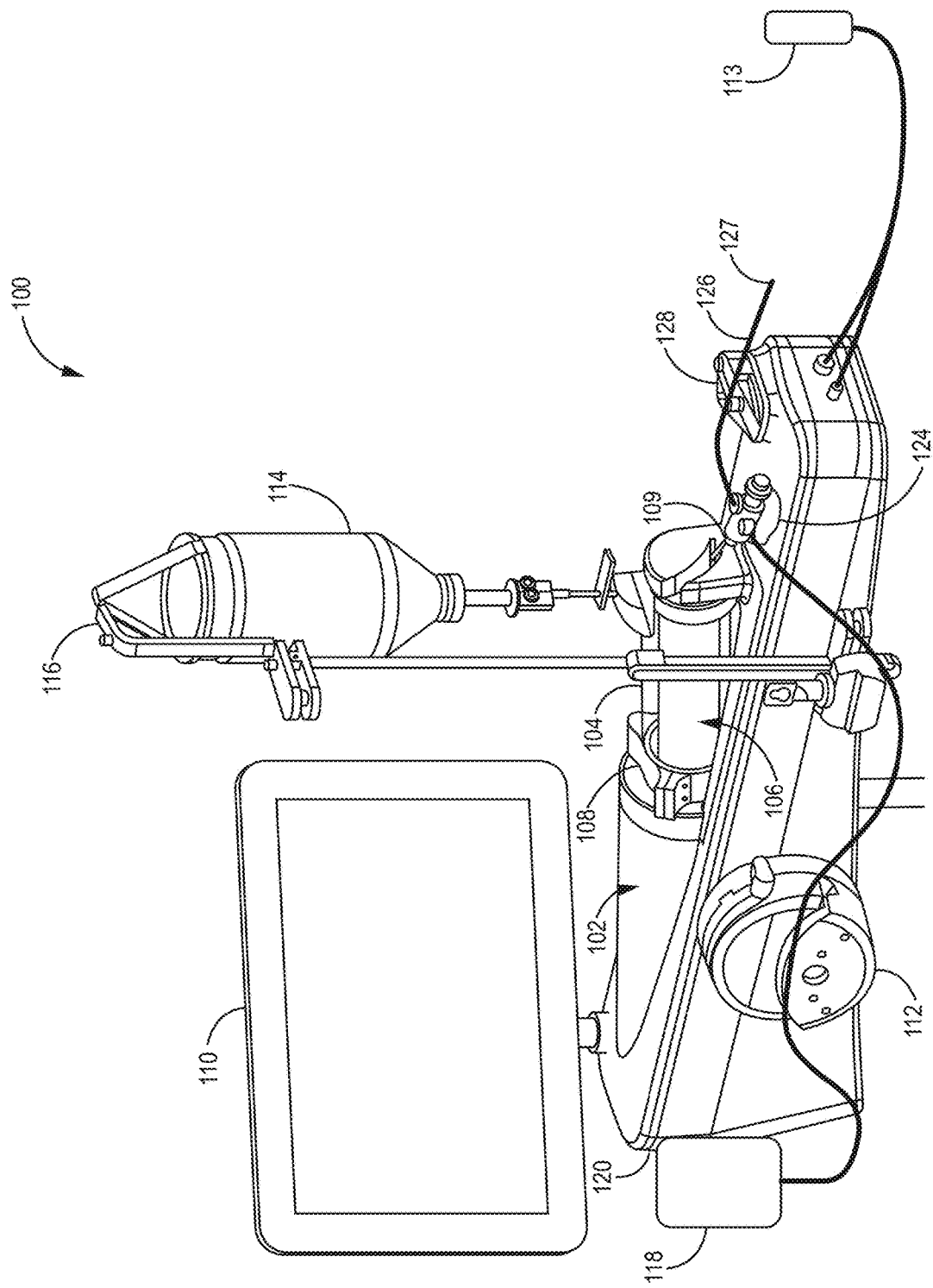
FIG. 1 is a perspective view of an embodiment of a fluid injector.

FIG. 1 shows a perspective view of an exemplary embodiment of a fluid injector 100. In operation, the fluid injector 100 can inject a quantity of fluid into a patient, for instance into a vessel of a patient via a catheter. The fluid injected by the fluid injector 100 can be, for example, a contrast fluid, a non-contrast fluid (e.g., saline), or a combination thereof. By injecting a quantity of fluid into a patient, the fluid injector 100 can facilitate a variety of medical diagnostic and/or interventional procedures, including the collection of image data representing an anatomical region of interest. Such procedures can include, as examples, optical coherence tomography (OCT) imaging, intravascular ultrasound (IVUS) imaging, computed tomography (CT) imaging, magnetic resonance (MM) imaging, angiographic procedures, and interventional device procedures/placements.

The illustrated fluid injector 100 includes a drive assembly housing 102 and a sleeve 104. The sleeve 104 can be secured to the drive assembly housing 102. For example, the drive assembly housing 102 can include an opening, and the sleeve 104 can be secured to the drive assembly housing 102 at, or near, such opening. The sleeve 104 may extend out from the drive assembly housing 102 and may be configured to receive and secure thereat a fluid reservoir 106. Although the illustrated example in FIG. 1 shows one fluid reservoir 106, other fluid injector 100 embodiments can include two (or more) fluid reservoirs 106 and a corresponding number of sleeves 104. The fluid reservoir 106 can define an internal reservoir volume that includes a plunger 108. At least a portion of a drive assembly can be housed within the drive assembly housing 102. The drive assembly can be configured to pressurize fluid within the internal reservoir volume. For instance, the drive assembly may couple to the plunger 108, such as at the opening in the drive assembly housing 102, and drive the plunger 108 within the internal reservoir volume of the fluid reservoir 106. As the plunger 108 is progressively driven within the fluid reservoir 106, fluid within the internal reservoir volume can be pressurized and output from the fluid reservoir 106 along a fluid line 109 leading to a patient. In certain applications of the fluid injector 100, output fluid, such as contrast media, can be pressurized anywhere from 1000-1500 psi (e.g., 1200 psi). In embodiments that include two (or more) fluid reservoirs 106, a corresponding number of drive assemblies can be housed within the drive assembly housing 102 for pressurizing fluid within each fluid reservoir.

The illustrated embodiment of the fluid injector 100 includes several features that can be useful in pressurizing and delivering fluid during operation. For example, the fluid injector 100 can include a control panel 110. The control panel 110 can provide a user interface for various operational aspects. For example, the control panel 110 can be utilized by an operator to set up various parameters and/or protocols to be used for a given fluid injection procedure. The control panel 110 can also be used to initialize the fluid injector 100 (e.g., to prepare it for a patient fluid injection), or to activate certain features or sequences of operation. In some cases, as shown here, a hand controller 113 can be coupled to the control panel 110 and used by an operator to remotely input injection-related signals to the fluid injector 100. The control panel 110 may also provide status information, including information related to past or currently ongoing injection procedures as well as any appropriate alerts. The control panel 110 can include an imaging engine having one or more processors for controlling operation of the powered fluid injector 100. Such processors can also communicate with and/or control other components, such as the drive assembly, a peristaltic pump 112, when present, and/or any sensors and detectors (e.g., air detection sensor 126 and/or hemodynamic pressure transducer 128) connected to the fluid injector 100.

The fluid injector 100 can also include one or more components useful for supplying fluid to be used in an injection procedure. In applications where two fluids are to be injected into a patient, a fluid supply container 114 and a fluid supply container 118 can be fluidly coupled to the fluid injector 100. As one example, the fluid supply container 114 can be a contrast fluid supply container, and the fluid supply container 118 can be a saline fluid supply container. As shown here, a holder 116 can be included at the fluid injector 100 to hold the fluid supply container 114, and a holder 120 can be included at the fluid injector 100 to hold the fluid supply container 118. In the illustrated embodiment, fluid (e.g., contrast fluid) from the fluid supply container 114 can be supplied to the fluid reservoir 106 for use during an injection procedure. For example, fluid from the fluid supply container 114 can be drawn into the fluid reservoir 106 when the plunger 108 is being retracted (e.g., moved in a direction toward the drive assembly housing 102) and thereby refill the internal reservoir volume. In the illustrated embodiment, the fluid injector 100 includes a peristaltic pump 112 for delivering fluid from the fluid supply container 118 to the patient. Often times, the peristaltic pump 112 may be used to deliver non-contrast fluid, such as saline, at a lower pressure than that at which the drive assembly delivers contrast fluid from the reservoir 106. Though, as noted, in other embodiments the fluid injector 100 can include a second fluid reservoir 106 and use a corresponding drive assembly housed within the drive assembly housing 102 to pressurize and deliver non-contrast fluid from the fluid supply container 118. In some such embodiments, a second fluid reservoir 106 and corresponding drive assembly may be present lieu of the peristaltic pump 112.

A manifold connector 124 can be included to selectively place one of the fluid reservoir 106 and peristaltic pump 112 (or second fluid reservoir 106, depending on the embodiment) in communication with the patient. Accordingly, the manifold connector 124 can selectively place fluid from the fluid supply container 114 and fluid from the fluid supply container 118 in communication with the patient. For example, in response to a change in pressure, the manifold connector 124 can switch from allowing fluid communication to the patient from one of the fluid reservoir 106, and fluid supply container 114, to the other of the peristaltic pump 112 (or second fluid reservoir 106, depending on the embodiment) and fluid supply container 118. A patient interface connector 127 can also be included, for instance at the fluid line 109, to selectively permit fluid, such as fluid from the manifold connector 124, to pass therethrough, such as to a patient interfacing component (e.g., catheter, such as an injection catheter). The patient interface connector 127 can include a valve that is configured to selectively permit fluid to be communicated through the patient interface connector 127.

As noted, one or more sensors can be connected to the fluid injector 100 to provide information relating to an injection. In the illustrated embodiment, the air detection sensor 126 and hemodynamic pressure transducer 128 are connected to the fluid injector 100. The air detection sensor 126 can be configured to detect the presence of air (e.g., one or more air bubbles) in one or more components. As shown here, the air detection sensor 126 can be configured to detect the presence of air in the fluid line 109 at a location between an outlet of the manifold connector 124 and the patient. For instance, the fluid line 109 can have an air detection interface at which the air detection sensor 126 can detect the presence of air in the fluid line 109. The air detection sensor 126 can output a signal at the fluid injector 100 when such air is detected, and the fluid injector 100 can take a corresponding action, such as stopping an injection and/or providing a warning to a user. The hemodynamic pressure transducer 128 can be configured to measure pressure, for instance in the fluid line 109. When the manifold connector 124 is open such that the hemodynamic pressure transducer 128 is in fluid communication with the patient, the hemodynamic pressure transducer 128 can output a signal corresponding to a pressure internal to a patient.

Preparing a fluid injector for use can require a number of steps. Because some components used in a fluid injection are routinely replaced (e.g., after a single use), preparing a fluid injector for use can include frequently replacing and appropriately connecting new components. Once these new components have been connected, preparing a fluid injector may also include an air purge process (e.g., before introducing fluid from the fluid injector 100 into the patient). The air purge process can remove any air contained in the injection components so that air is not introduced into a patient during an injection. These steps can consume significant time and require detailed attention. However, certain fluid injector applications can be time-sensitive and may make it difficult in real-time to devote the attention to detail needed to properly prepare the fluid injector for such applications.

The present disclosure describes embodiments that can facilitate more efficient workflow in preparing a fluid injector for use. Embodiments disclosed herein can, for instance, allow certain components to be set up at a fluid injector in advance of an application in which the fluid injector is needed while preserving the sterility of other components. More specifically, embodiments can allow various components to be connected to a fluid injector and facilitate an air purge process in advance of an application in which the fluid injector is needed. At the same time, a packaging container can preserve a sterile environment around other components while necessary connections are made and the air purge process is performed. Then, when the need to use the fluid injector later arises, removal of the packaging container and connection to a patient component (e.g., an injection catheter) may be the only preparation needed at that time to use the fluid injector. Accordingly, when the need to use the fluid injector arises, embodiments within the scope of the present disclosure can reduce the time needed to prepare for a fluid injection. This can be particularly useful in time-sensitive injection applications.

Figure 2:
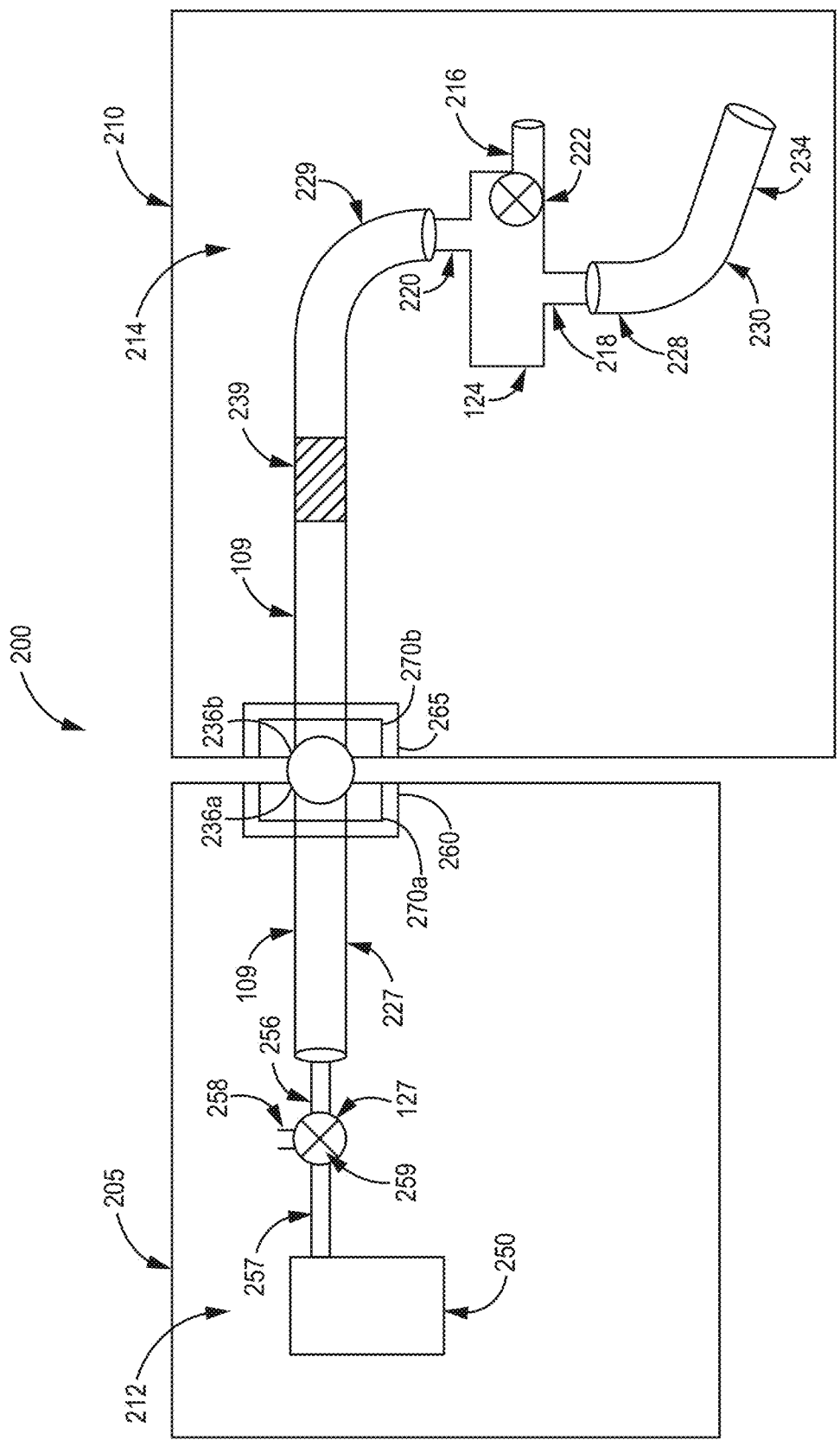
FIG. 2 is a schematic diagram showing an embodiment of an injection setup kit including an exemplary first packaging container and an exemplary second packaging container.
Figure 3:
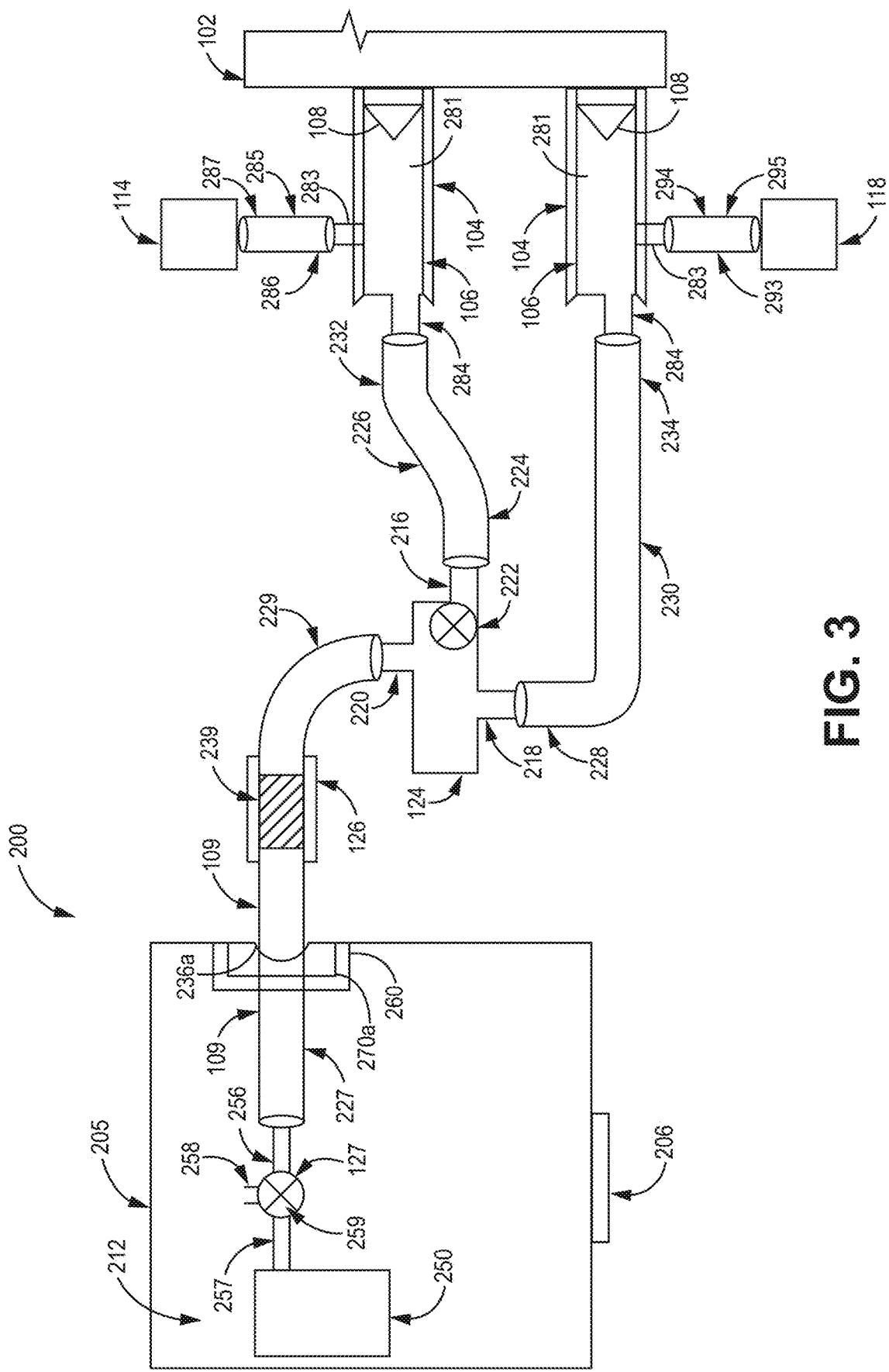
FIG. 3 is a schematic diagram showing the first packaging container of FIG. 2 but with the second packaging container of FIG. 2 removed.
Figure 4:
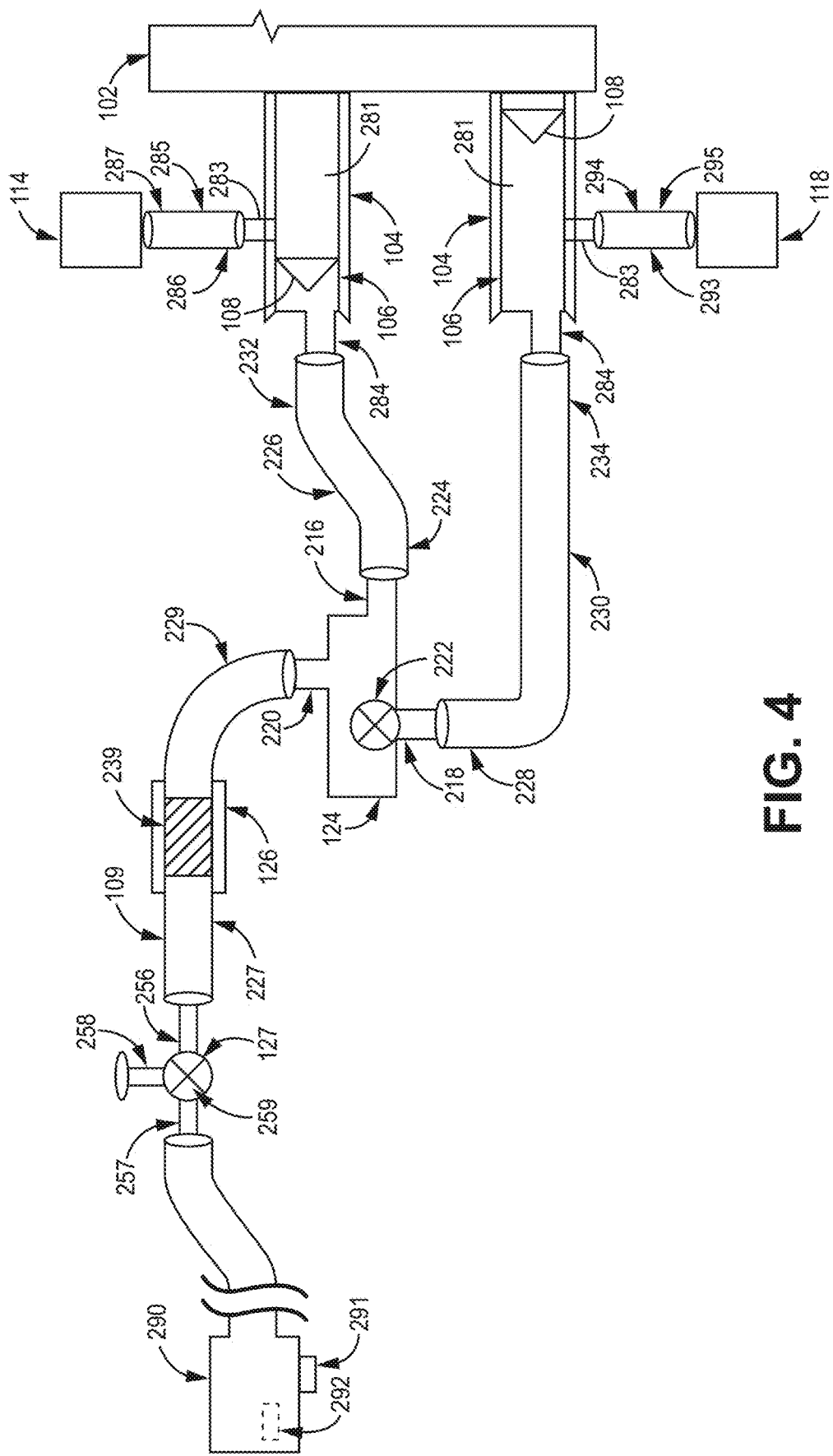
FIG. 4 is a schematic diagram showing both of the first and second packaging containers of FIG. 2 removed.

Taken together, FIGS. 2-4 show an exemplary sequence involving an injection setup kit and the corresponding setup of an injection system. This exemplary sequence starts with an initially provided injection setup kit in FIG. 2. It then proceeds, in FIG. 3, to the setup of components removed from one packaging container while another packaging container is maintained in a closed state. Then, in FIG. 4, an injection system is set up and ready for use.

FIG. 2 illustrates a schematic diagram of an embodiment of an injection setup kit 200. The injection setup kit 200, shown in FIG. 2, includes an embodiment of a first packaging container 205 and an embodiment of a second packaging container 210. Each of the first packaging container 205 and the second packaging container 210 can enclose one more components. The second packaging container 210 can be a separate packaging container from the first packaging container 205. Where the packaging containers 205, 210 are separate packaging containers, opening one of the first packaging container 205 and second packaging container 210 can allow one or more components enclosed therein to be removed while keeping one or more components enclosed in the other of the first packaging container 205 and second packaging container 210. As such, the injection setup kit 200 can allow certain components to be set up in a fluid injection system while preserving a sterile environment around other components that remain enclosed in the non-opened packaging container. Thus, the injection setup kit 200 can be configured to allow one packaging container, such as the second packaging container 210, to be opened and the components therein to be removed while maintaining a sterile environment in the other packaging container, such as the first packaging container 205.

The first packaging container 205 can define a first closed interior volume 212. The first packaging container 205 can enclose the first closed interior volume 212. In some embodiments, the first packaging container 205 encloses the first closed interior volume 212 such that one or more components within the first closed interior volume 212 cannot be removed until the first packaging container 205 is opened. In one embodiment, the first closed interior volume 212 may no longer be considered "closed" when action is taken to open, and thus physically alter the configuration of, the first packaging container 205. For example, the first packaging container 205 can be sealed around the first closed interior volume 212 to enclose the first closed interior volume 212. This can include the first packaging container 205 being sealed around a perimeter of any component extending outside of the first closed interior volume 212. In various embodiments, the first packaging container 205 can enclose the first closed interior volume 212 such that the first closed interior volume 212 defines a sterile environment.

Likewise, the second packaging container 210 can define a second closed interior volume 214. The second packaging container 210 can enclose the second closed interior volume 214. In some embodiments, the second packaging container 210 encloses the second closed interior volume 214 such that one or more components within the second closed interior volume 214 cannot be removed until the second packaging container 210 is opened. In one embodiment, the second closed interior volume 214 may no longer be considered "closed" when action is taken to open, and thus physically alter the configuration of, the second packaging container 210. For example, the second packaging container 210 can be sealed around the second closed interior volume 214 to enclose the second closed interior volume 214. This can include the second packaging container 210 being sealed around a perimeter of any component extending outside of the second closed interior volume 214. In various embodiments, the second packaging container 210 can enclose the second closed interior volume 214 such that the second closed interior volume 214 defines a sterile environment.

Depending on the particular embodiment, any number of a variety of components can be included within the first closed interior volume 212 and the second closed interior volume 214. The exemplary embodiment of the injection setup kit 200 described here includes components within the first closed interior volume 212 and the second closed interior volume 214 as suited for facilitating a more efficient workflow in preparing a fluid injector for use. In particular, the illustrated injection setup kit 200 can allow certain components to be set up at a fluid injector in advance of an application in which the fluid injector is needed while preserving the sterility of other components to be used later during operation of the fluid injection in conjunction with a patient procedure.

As shown in embodiment of FIG. 2, included within the first closed interior volume 212 of the first packaging container 205 is the patient interface connector 127. The patient interface connector 127 can include a patient interface inlet 256, a first patient interface outlet 257, and a valve 259. The valve 259 can be configured to selectively permit fluid to be communicated through the patient interface connector 127 from the patient interface inlet 256 to the first patient interface outlet 257. As shown in FIG. 2, the patient interface connector 127, while enclosed within the first closed interior volume 212, can be fluidly connected to the manifold connector 124. In particular, the patient interface inlet 256 can be fluidly connected to a manifold outlet 220 of the manifold connector 124 by the fluid line 109. Thus, within the first closed interior volume 212, the patient interface inlet 256 can be fluidly connected to the manifold outlet 220.

In some cases, as shown here, the patient interface connector 127 can further include a second patient interface outlet 258. In some examples, the second patient interface outlet 258 can serve as a flushing outlet. For instance, the second patient interface outlet 258 can provide an outlet to remove unwanted material from the fluid line 109, such as air bubbles or a fluid remaining therein from a previous operation (e.g., to remove residual contrast fluid remaining the line 109 before providing flushing fluid through the line 109). When the second patient interface outlet 258 is included, the valve 259 can be configured to selectively permit fluid to be communicated through the patient interface connector 127 from the patient interface inlet 256 to either of the first patient interface outlet 257 and the second patient interface outlet 258. For instance, after the first packaging container 205 has been opened, the valve 259 may be manually actuated by a user to place one of the first patient interface outlet 257 and the second patient interface outlet 258 in fluid communication with the patient interface inlet 256 while blocking fluid communication to the other of the first patient interface outlet 257 and the second patient interface outlet 258.

In some embodiments, the first closed interior volume 212 of the first packaging container 205 can further include a fluid collection receptacle 250. The fluid collection receptacle 250 can be configured to receive and hold fluid. Within the first closed interior volume 212, the first patient interface outlet 257 can be fluidly connected to the fluid collection receptacle 250. In particular, as shown in the illustrated embodiment of FIG. 2, the first patient interface outlet 257 can be fluidly connected to the fluid collection receptacle 250 such that the fluid collection receptacle 250 is in fluid communication with the manifold outlet 220 via the fluid line 109 and the patient interface connector 127. Accordingly, the fluid collection receptacle 250 can be configured to receive and hold fluid output from the manifold outlet 220. As described further herein, the fluid collection receptacle 250 can be used to collect fluid prior to injecting fluid within a patient. For instance, the fluid collection receptacle 250 can be used to collect fluid during setup of a fluid injection system, such as during an air purge process.

Also included within the first closed interior volume 212 of the first packaging container 205 can be a first fluid line end 227. The injection setup kit 200 can include the fluid line 109 having the first fluid line end 227 and a second fluid line end 229. The first fluid line end 227 can be connected to the patient interface inlet 256 within the first closed interior volume 212 of the first packaging container 205. The second fluid line end 229 can extend outside of the first closed interior volume 212 of the first packaging container 205. Thus, in this configuration, prior to opening the first packaging container 205, one portion of the fluid line 109 can be within the first closed interior volume 212 while another portion of the fluid line 109 can be outside of the first closed interior volume 212.

Included within the second closed interior volume 214 of the second packaging container 210 is the manifold connector 124, as shown in embodiment of FIG. 2. The manifold connector 124 can include a first manifold inlet 216, a second manifold inlet 218, and a manifold outlet 220. The manifold connector 124 can be configured to selectively place one of the first manifold inlet 216 and the second manifold inlet 218 in fluid communication with the manifold outlet 220.

In one embodiment, to facilitate this selective fluid communication, the manifold connector 124 can include a manifold valve 222. The manifold valve 222 can be configured to move between one position that blocks the first manifold inlet 216 and another position that blocks the second manifold inlet 218. For example, the manifold valve 222 can be configured to move between such positions in response to a change in fluid pressure at the manifold connector 124. In this way, the manifold valve 222 can be configured to move, in response to a change in pressure at the manifold connector 124, between a first manifold valve position (shown, e.g., in FIG. 2) in which the manifold valve 222 blocks fluid communication from the first manifold inlet 216 to the manifold outlet 220 and a second manifold valve position (shown, e.g., in FIG. 4) in which the manifold valve 222 blocks fluid communication from the second manifold inlet 218 to the manifold outlet 220. In some embodiments, the manifold valve 222 can be biased (e.g., via a biasing member, such as a spring) to the first manifold valve position. Then, when a pressure at the first manifold inlet 216 reaches a predetermined threshold the biasing force at the manifold valve 222 can be overcome causing the manifold valve 222 to move to the second manifold valve position.

In some embodiments, the second closed interior volume 214 of the second packaging container 210 can further include an air detection interface 239. The air detection interface 239 can be configured to facilitate detection of the presence of air in the fluid line 109. For instance, the air detection interface 239 can be configured to interface with the air detection sensor 126 and allow the air detection sensor 126 to detect the presence of air in the fluid line 109. The air detection sensor 126 can thus detect the presence of air (e.g., one or more air bubbles), such as in the fluid line 109 at the air detection interface 239, and output a signal when air is detected. The air detection interface 239 can be located downstream of the manifold outlet 220, as shown in FIG. 2. In particular, in the illustrated embodiment, the air detection interface 239 is included at the fluid line 109. In one example, the air detection interface 239 can be a region of the fluid line 109. In such an example, the air detection interface 239 can be a region of the fluid line 109 that is both downstream of the manifold outlet 220 and within the second closed interior volume 214.

In one embodiment, such as that illustrated in FIG. 2, the second closed interior volume 214 of the second packaging container 210 can also include a flushing fluid line 230. The flushing fluid line 230 can have a first flushing fluid line end 228 and a second flushing fluid line end 234. The first flushing fluid line end 228 can be connected to the second manifold inlet 218 within the second closed interior volume 214 of the second packaging container 210. As shown in the illustrated embodiment, both the first flushing fluid line end 228 and the second flushing fluid line end 234 can be within the second closed interior volume 214. In another embodiment, the second closed interior volume 214 of the second packaging container 210 can additionally include a contrast fluid line connected to the first manifold inlet 216. Though, in some embodiments, there may not be any fluid line connected to either of the first and second manifold inlets 216, 218 within the second closed interior volume 214 of the second packaging container 210.

Also included within the second closed interior volume 214 of the second packaging container 210 can be the second fluid line end 229 of the fluid line 109. The second fluid line end 229 can be connected to the manifold outlet 220 of the manifold connector 124. Thus, as shown in FIG. 2, the second fluid line end 229 extends outside of the first closed interior volume 212 of the first packaging container 205 and is connected to the manifold outlet 220 outside of the first closed interior volume 212 of the first packaging container 205. In particular, as shown here, the second fluid line end 229 extends outside of the first closed interior volume 212 of the first packaging container 205 and extends into the second closed interior volume 214 of the second packaging container 210 and is connected to the manifold outlet 220 within the second closed interior volume 214 of the second packaging container 210.

To facilitate the extension of one or more component portions, such as a portion of the fluid line 109, outside of the first closed interior volume 212, the first packaging container 205 can include one or more apertures 236*a*. For instance, the first packaging container 205 can define the aperture 236*a* through which at least the second fluid line end 229 of the fluid line 109 extends outside of the first closed interior volume 212 of the first packaging container 205. In instances where more than one component portion extends outside of the first closed interior volume 212, the first packaging container 205 can define an aperture for each such component portion extending outside of the first closed interior volume 212. Though in instances where more than one component portion extends outside of the first closed interior volume 212, the first packaging container 205 can define a single, common aperture, such as the aperture 236*a*, through which each component portion extends outside of the first closed interior volume 212.

The aperture 236*a* can be sized to close (e.g., in a sealing manner) the first closed interior volume 212 at the one or more portions extending outside of the first closed interior volume 212. For example, the aperture 236*a* can be sized to close the first closed interior volume 212 around an outer perimeter surface of the fluid line 109. In this example, the first packaging container 205 can contact the outer perimeter surface of the fluid line 109 at the location of the aperture 236*a*. The aperture 236*a* can thus be sized to allow the intended component(s), such as the fluid line 109, to extend out from the first closed interior volume 212 but to prevent other components from extending out from the first closed interior volume 212. For instance, the aperture 236*a* can be sized to prevent the patient interface connector 127 from extending outside of the first closed interior volume 212.

In the embodiment illustrated in FIG. 2, one or more component portions extending outside of the first closed interior volume 212 can extend into the second closed interior volume 214 of the second packaging container 210. For example, as shown in FIG. 2, a portion of the fluid line 109 extends outside of the first closed interior volume 212 and into the second closed interior volume 214. As such, the second fluid line end 229 can extend into the second closed interior volume 214.

To facilitate the extension of one or more component portions, such as a portion of the fluid line 109, into the second closed interior volume 214, the second packaging container 210 can include one or more apertures 236*b*. For instance, the second packaging container 210 can define the aperture 236*b* through which at least the second fluid line end 229 extends into the second closed interior volume 214 of the second packaging container 210. In instances where more than one component portion extends into the second closed interior volume 214, the second packaging container 210 can define an aperture for each such component portion extending into the second closed interior volume 214. Though in instances where more than one component portion extends into of the second closed interior volume 214, the second packaging container 210 can define a single, common aperture, such as the aperture 236*b*, through which each component portion extends into the second closed interior volume 214.

In one embodiment, the aperture 236*b*, when included, can correspond respectively to the aperture 236*a*, when included. For instance, the aperture 236*b* can be sized to close the second closed interior volume 214 at the one or more component portions extending into the second closed interior volume 214, and the aperture 236*b* can be sized the same as the corresponding aperture 236*a*. In the illustrated embodiment, the aperture 236b can be sized to close the second closed interior volume 214 around the outer perimeter surface of the fluid line 109.

The injection setup kit 200 shown in FIG. 2 includes the first packaging container 205 interfacing with the second packaging container 210. In this illustrated embodiment, the aperture 236a of the first packaging container 205 interfaces with the aperture 236b of the second packaging container 210. The aperture 236a included in the first packaging container 205 can be aligned with the aperture 236b included in the second packaging container 210.

In some embodiments, the first and second packaging containers 205, 210 can be removably coupled together. For example, the first and second packaging containers 205, 210 can be removably coupled together at a common packaging area where the packaging containers 205, 210 interface. In the illustrated embodiment, the first packaging container 205 includes a face plate 260 and the second packaging container 210 includes a face plate 265. The face plates 260, 265 may be made of a different (e.g., more ridged) material than that of the packaging containers 205, 210. As shown here, the face plate 260 can be located over an area of the first packaging container 205 having the aperture 236a, and in some cases it may be the face plate 260 that defines the aperture 236a in the first packaging container 205. And, the face plate 265 can be located over an area of the second packaging container 210 having the aperture 236b, and in some cases it may be the face plate 265 that defines the aperture 236b in the second packaging container 210. The face plate 265 of the second packaging container 210 can be configured to removably couple to the face plate 260 of the first packaging container 205. For instance, the face plate 265 can include a connection element 270b that is configured to removably couple to a corresponding connection element 270a included at the face plate 260. The corresponding connection elements 270a, 270b can be any of a variety of suitable connection elements, such as interference fit members (e.g., buttons or other slide or snap fit members). In other instances, instead of, on in addition to, distinct connection elements, the face plates 260, 265 can include an adhesive or tear away coupling therebetween.

FIG. 3 illustrates an exemplary schematic diagram showing the first packaging container 205, as described previously, but with the second packaging container removed. As shown in FIG. 3, when the second packaging container is opened, those components removed from the second packaging container can be connected to corresponding components of an injection system.

When the second packaging container is opened and removed from the injection setup kit, the first packaging container 205 can be configured to continue to enclose the first closed interior volume 212 and those components included within the first closed interior volume 212. For example, the first packaging container 205 may include an attachment member 206 that is configured to allow the first packaging container 205 to be removably secured to the fluid injector, such as at the drive assembly housing 102. In one embodiment, the fluid injector may have a corresponding attachment member configured to removably receive the attachment member 206. This can allow the first packaging container to be temporarily placed in a known, convenient location while those components removed from the second packaging container are connected to the injector and the injection system is being set up.

In this way, the second packaging container can be opened and removed from the injection setup kit without opening the first packaging container 205. This can be the case where the first and second packaging containers are separate containers. And, when the first and second packaging containers interface and are removably coupled together, the removable coupling therebetween (e.g., via the face plates) can be configured to allow the second packaging container to be removed without opening the first packaging container 205. For example, when the second packaging container is removed from the injection setup kit, the first packaging container 205 can be configured to maintain a sterile environment within the first closed interior volume 212. In addition, as shown here, when the second packaging container is removed from the injection setup kit, the first packaging container 205 can be configured to maintain the first fluid line end 227 connected to the patient interface inlet 256 within the first closed interior volume 212 of the first packaging container 205.

The second packaging container can be opened, and one or more components included within the second packaging container can be removed and connected to one or more corresponding fluid injection system components. For example, opening the second packaging container can include introducing the interior volume defined by the second packaging container to an ambient environment such that the second packaging container no longer defines a second closed interior volume when opened. At the same time, opening, and removing, the second packaging container can include maintaining the closed interior volume 212 and a sterile environment within the closed interior volume 212 of the first packaging container 205.

In the illustrated embodiment, opening the second packaging container can include removing the manifold connector 124 from the second packaging container. The manifold connector 124, as removed from the second packaging container, can be connected to the second fluid line end 229 while the first fluid line end 227 is within the first closed interior volume 212 of the first packaging container 205. Thus, removing the manifold connector 124 from the second packaging container can include removing the second fluid line end 229 from the second packaging container. In other embodiments, the second fluid line end 229 may be disconnected from the manifold connector 124 while enclosed within the second packaging container, and a user may connect the second fluid line end 229 to the manifold connector 124 after the second packaging container is removed. As shown here, when the manifold connector 124 is removed from the second packaging container, the fluid line 109 can extend through the aperture 236a included at the first packaging container 205, and the first fluid line end 227 can be connected to the patient interface inlet 256 within the first closed interior volume 212.

After opening the second packaging container and removing the manifold connector 124, the manifold connector 124 can be connected to a fluid injector, such as fluidly connected to one or more fluid supply containers 114, 118. In particular, after opening the second packaging container and removing the manifold connector 124, the manifold connector 124 can be connected to at least one fluid reservoir 106. In the illustrated embodiment, the manifold connector 124 is fluidly connected to two fluid reservoirs 106. As shown in FIG. 3, the first manifold inlet 216 can be fluidly connected to one fluid reservoir 106 and the second manifold inlet 218 can be fluidly connected to another fluid reservoir 106. Specifically, the first manifold inlet 216 can be fluidly connected to one fluid reservoir by a contrast fluid line 226. The contrast fluid line 226 can have a first contrast fluid line end 224 and a second contrast fluid line end 232. The first contrast fluid line end 224 can be connected to the first manifold inlet 216 and the second contrast fluid line end 232 can be connected to a reservoir outlet 284 of the fluid reservoir 106. And, the second manifold inlet 218 can be fluidly connected to the other fluid reservoir 106 by the flushing fluid line 230. The first flushing fluid line end 228 can be fluidly connected to the second manifold inlet 218 and the second flushing fluid line end 234 can be fluidly connected to a reservoir outlet 284 of the other fluid reservoir 106.

As described previously, in some embodiments the second packaging container can include the flushing fluid line 230. In these embodiments, opening the second packaging container can include removing the flushing fluid line 230 from the second packaging container. In these embodiments, the first flushing fluid line end 228 is fluidly connected to the second manifold inlet 218 prior to opening the second packaging container. Thus, for these embodiments, connecting the second manifold inlet 218 to the fluid injector may only include fluidly connecting the second flushing fluid line end 234 to the reservoir outlet 284 of the other fluid reservoir 106.

In addition, in the illustrated embodiment, opening the second packaging container can include removing the air detection interface 239 from the second packaging container. For instance, when the air detection interface 239 is at the region of the fluid line 109 as in the illustrated embodiment, the air detection interface 239 can be removed from the second packaging container when the portion of the fluid line 109 is removed from the second packaging container. As shown in FIG. 3, when the air detection interface 239 is removed from the second packaging container, the air detection interface 239 can be positioned to interface with the air detection sensor 126 such that the presence of air in the fluid line 109 can be detected.

When one or more components removed from the second packaging container are connected to corresponding components of an injection system, such as shown in FIG. 3, further action may be taken to prepare the injection system for later use with a patient. Such further action may be taken while certain components remain enclosed within the first closed interior volume 212 of the first packaging container 205. As one example, to prepare the injection system for later use with a patient, when one or more components removed from the second packaging container are connected to components of an injection system and while certain components remain enclosed within the first closed interior volume 212, one or more air purge actions can be taken.

After connecting the manifold connector 124 to the fluid injector, such as shown in FIG. 3, fluid can be conveyed through the manifold connector 124, fluid line 109, and patient interface connector 127.

For example, after connecting the first manifold inlet 216 to the contrast fluid supply container 114, contrast fluid can be delivered from the contrast fluid supply container 114, along the contrast fluid line 226, and to the fluid collection receptacle 250 that is within the closed interior volume 212 of the first packaging container 205. This can include conveying contrast fluid through the manifold connector 124, the fluid line 109, and the patient interface connector 127, with the first fluid line end 227 and the patient interface connector 127 fluidly connected within the closed interior volume 212. For instance, the manifold valve 222 can be in the position that blocks the second manifold inlet 218, and contrast fluid can be conveyed through the first manifold inlet 216 and out the manifold outlet 220. Also, the valve 259 can be in a position to permit fluid to be communicated from the patient interface inlet 256 to the first patient interface outlet 257 and then into the fluid collection receptacle 250. In the illustrated embodiment, the contrast fluid supply container 114 is fluidly connected to the fluid reservoir 106 via a contrast supply fluid line 285 that has a first contrast supply fluid line end 286 fluidly connected to a reservoir inlet 283 and a second contrast supply fluid line end 287 fluidly connected to the contrast fluid supply container 114. Conveying contrast fluid along the contrast fluid line 226 to the fluid collection receptacle 250 can act to purge air from components connected on the contrast fluid pathway, including those components that are within the closed interior volume 212.

In addition, after connecting the second manifold inlet 218 to the flushing fluid supply container 118, flushing fluid can be delivered from the flushing fluid supply container 118, along the flushing fluid line 230, and to the fluid collection receptacle 250 that is within the closed interior volume 212 of the first packaging container 205. This can include conveying flushing fluid through the manifold connector 124, the fluid line 109, and the patient interface connector 127, with the first fluid line end 227 and the patient interface connector 127 fluidly connected within the closed interior volume 212. For instance, the manifold valve 222 can be in the position that blocks the first manifold inlet 216, and flushing fluid can be conveyed through the second manifold inlet 218 and out the manifold outlet 220. Also, the valve 259 can be in a position to permit fluid to be communicated from the patient interface inlet 256 to the first patient interface outlet 257 and then into the fluid collection receptacle 250. In the illustrated embodiment, the flushing fluid supply container 118 is fluidly connected to the fluid reservoir 106 via a flushing fluid supply fluid line 293 that has a first flushing supply fluid line end 294 fluidly connected to a reservoir inlet 283 and a second flushing supply fluid line end 295 fluidly connected to the flushing fluid supply container 118. Conveying flushing fluid along the flushing fluid line 230 to the fluid collection receptacle 250 can act to purge air from components connected on the flushing fluid pathway, including those components that are within the closed interior volume 212.

The ability to connect various components and purge air from these components can allow a fluid injection system to be set up prior to later use with a patient. This advance setup can be helpful in reducing the time and effort needed to prepare a fluid injection system at a time when it is needed. Moreover, the embodiments described herein may maintain certain patient interfacing components of the injection system within a sterile environment, such as within the first packaging container 205, while this advance setup takes place. In this way, when the injection system is needed for use with a patient, the setup time and effort is greatly reduced. This can allow various diagnostic procedures to be performed in conjunction with the injection system sooner and with less user burden in setup. This may help to improve the outcome of such diagnostic procedures.

When a need arises to perform an injection, the first packaging container can be removed, and an injection catheter can be connected. Since embodiments disclosed herein can allow various setup steps to be performed in advance, these setup steps may not need to be performed when the need for the injection arises. For example, in one embodiment, the only step needed may be removing the first packaging container. In another embodiment, the only steps needed may be removing the first packaging container and connecting an injection catheter. In a further embodiment, the only steps needed may be removing the first packaging container, removing the fluid collection receptacle, and connecting an injection catheter.

FIG. 4 illustrates an exemplary schematic diagram showing both the first packaging container and the second packaging container removed. As shown in FIG. 4, one or more components removed from the second packaging container can be connected to corresponding components of an injection system, as described in reference to FIG. 3. And, as also shown in FIG. 4, one or more components removed from the first packaging container can be connected to an injection catheter. For example, the first packaging container can be opened both after the second packaging container has been opened and after one or more components previously within the second packaging container are connected to components of an injection system. In some cases, contrast and/or flushing fluid can be delivered (e.g., as part of an air purge process) through one or more components, previously within the second packaging container and connected to components of an injection system, prior to opening the first packaging container.

For example, in the illustrated embodiment, after delivering contrast fluid to the fluid collection receptacle, the first packaging container can be opened. Opening the first packaging container can include removing the patient interface connector 127 from the first packaging container. Because the patient interface connector 127 is connected to the first fluid line end 227, removing the patient interface connector 127 from the first packaging container can include removing the first fluid line end 227 from the first packaging container. In addition, opening the first packaging container can include removing the fluid collection receptacle from the first packaging container.

As shown in FIG. 4, once the first packaging container is opened, an injection catheter 290 can be fluidly connected to one or more components previously enclosed within the first packaging container. For example, in the illustrated embodiment, after opening the first packaging container the patient interface connector 127 can be fluidly connected to the injection catheter 290. In this example, this can place each of the fluid reservoirs 106, and associated fluid supply containers 114, 118, in fluid communication with the injection catheter 290. In embodiments where the fluid collection receptacle is included within the first packaging container, for instance to hold fluid received prior to opening the first packaging container, the fluid collection receptacle can be removed after opening the first packaging container. For instance, the fluid collection receptacle can be removed from the first patient interface outlet 257, and the injection catheter 290 can be connected at the first patient interface outlet 257. Once disconnected, the fluid collection receptacle may be discarded.

The injection catheter 290 can be configured to be positioned at, or within, a patient and to deliver fluid to the patient. After fluidly connecting the injection catheter 290, such as to the patient interface connector 127, one or more fluids can be delivered from the fluid injector to the injection catheter 290. For example, contrast fluid can be delivered from the fluid reservoir 106, through the manifold connector 124, and along the fluid line 109 to the injection catheter 290. As another example, flushing fluid can be delivered from the other fluid reservoir 106, through the manifold connector 124, and along the fluid line 109 to the injection catheter 290.

In the example shown here, the injection catheter 290 includes a fluid delivery port 291. The fluid delivery port 291 can be configured to deliver to the patient (e.g., at a region of interest within the patient) fluid received at the injection catheter 290 from the one or more components shown in FIG. 4.

Also in the example shown here, the injection catheter 290 includes an imaging element 292. The imaging element 292 can be configured to collect image data and convey the image data to an imaging engine for processing and/or display. In some cases, the introduction of fluid via the injection catheter 290 can improve the quality of image data collected by the imaging element 292.

Figure 5:
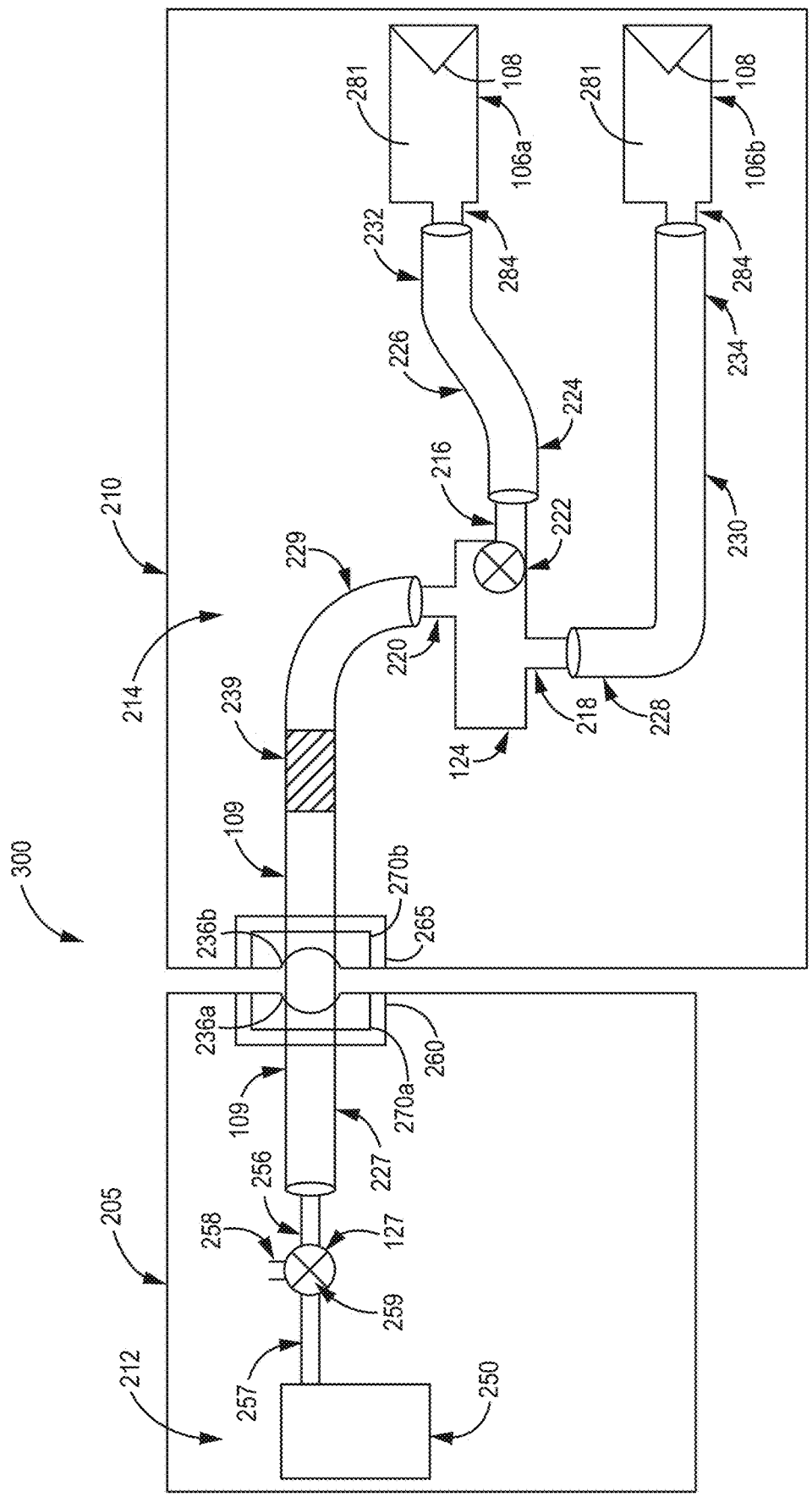
FIG. 5 is a schematic diagram showing another embodiment of an injection setup kit including an exemplary first packaging container and an exemplary second packaging container.

FIG. 5 is a schematic diagram illustrating another embodiment of an injection setup kit 300. The injection setup kit 300 is similar to the injection setup kit 200 except that additional components are included in the second closed interior volume 214 of the second packaging container 210. Thus, reference characters shown in FIG. 5 for the injection setup kit 300 are used to convey the presence of like elements described previously with respect to the injection setup kit 200.

The components included within the first closed interior volume 212 of the first packaging container 205 in the injection setup kit 300 are the same as those previously described for the injection setup kit 200. Namely, the first closed interior volume 212 of the first packaging container 205 in the injection setup kit 300 includes the patient interface connector 127, first fluid line end 227, and fluid collection receptacle 250. The patient interface connector 127 is fluidly connected to both the fluid collection receptacle 250 and the first fluid line end 227 within the first closed interior volume 212.

The second closed interior volume 214 of the second packaging container 210 in the injection setup kit 300 includes the manifold connector 124. As illustrated in FIG. 5, the second closed interior volume 214 of the second packaging container 210 in the injection setup kit 300 also includes the contrast fluid line 226, the flushing fluid line 230, a first fluid reservoir 106a, and a second fluid reservoir 106b. Each of the first fluid reservoir 106a and the second fluid reservoir 106b defines an internal reservoir volume 281. The internal reservoir volume 281 of each of the first fluid reservoir 106a and the second fluid reservoir 106b can include the plunger 108. Each of the first fluid reservoir 106a and the second fluid reservoir 106b can also include a reservoir outlet 284 (and, in some embodiments, the reservoir inlet 283 as shown previously).

The contrast fluid line 226 has the first contrast fluid line end 224 and the second contrast fluid line end 232. The first contrast fluid line end 224 is connected to the first manifold inlet 216 within the second closed interior volume 214 of the second packaging container 210. And, the second contrast fluid line end 232 is connected to the first fluid reservoir 106a within the second closed interior volume 214 of the second packaging container 210.

The flushing fluid line 230 has the first flushing fluid line end 228 and the second flushing fluid line end 234. The first flushing fluid line end 228 is connected to the second manifold inlet 218 within the second closed interior volume 214 of the second packaging container 210. And, the second flushing fluid line end 234 is connected to the second fluid reservoir 106b within the second closed interior volume 214 of the second packaging container 210.

When second packaging container 210 is opened, the fluid reservoirs 106a, 106b, contrast fluid line 226, flushing fluid line 230, manifold connector 124, and second fluid line end 229 can all be removed from the second closed interior volume 214 in a fluidly connected state. When these components are removed from the second closed interior volume 214, the manifold connector 124 can be in fluid communication with the patient interface connector 127 via the fluid line 109. The fluid reservoirs 106a, 106b can be secured at respective sleeves 104 included at the drive assembly housing 102 of a fluid injector. Securing the fluid reservoirs 106a, 106b at the respective sleeves 104 can include coupling the respective plunger 108 to a drive assembly of the fluid injector such that the drive assembly can move the plunger 108 within the respective internal reservoir volume 281. The fluid purge process can then be carried out in a manner as described with respect to the injection setup kit 200.

By including at least one fluid reservoir 106a, 106b within the second closed interior volume 214 of the second packaging container 210, the injection setup kit 300 illustrating in FIG. 5 may be able to further facilitate efficient fluid injection system setup and initialization (e.g., air purge) prior to use of the fluid injection system in a patient procedure. At the same time, the injection setup kit 300 can preserve a sterile environment for certain components (e.g., those within the first closed interior volume 212 of the first packaging container 205) until the time comes for using the fluid injection system in a patient procedure.

While FIGS. 2-5 have been described with reference to embodiments having a first packaging container and a second packing container, other embodiments within the scope of the present disclosure can include more than two packaging containers. For example, some embodiments can include a third packaging container in addition to the first packaging container and the second packaging container. The third packaging container can define a third closed interior volume that includes at least one component. In such embodiments, any one or more components disclosed herein can be in the third packaging container instead of the first packaging container and/or the second packaging container. Each of the first, second, and third packaging container can define a closed interior volume that includes at least one component disclosed herein.

In one illustrative example of an embodiment that includes first, second, and third packaging containers, the third closed interior volume of the third packaging container can include the fluid collection receptacle. In this same illustrative embodiment, each of the first closed interior volume of the first packaging container and the second closed interior volume of the second packaging container can include one or more components as disclosed previously herein. For instance, the third closed interior volume of the third packaging container can include the fluid collection receptacle, and the first patient interface outlet can be connected to the fluid collection receptacle within the third closed interior volume. In this instance, the patient interface inlet can be included within the first closed interior volume.

Figure 6:
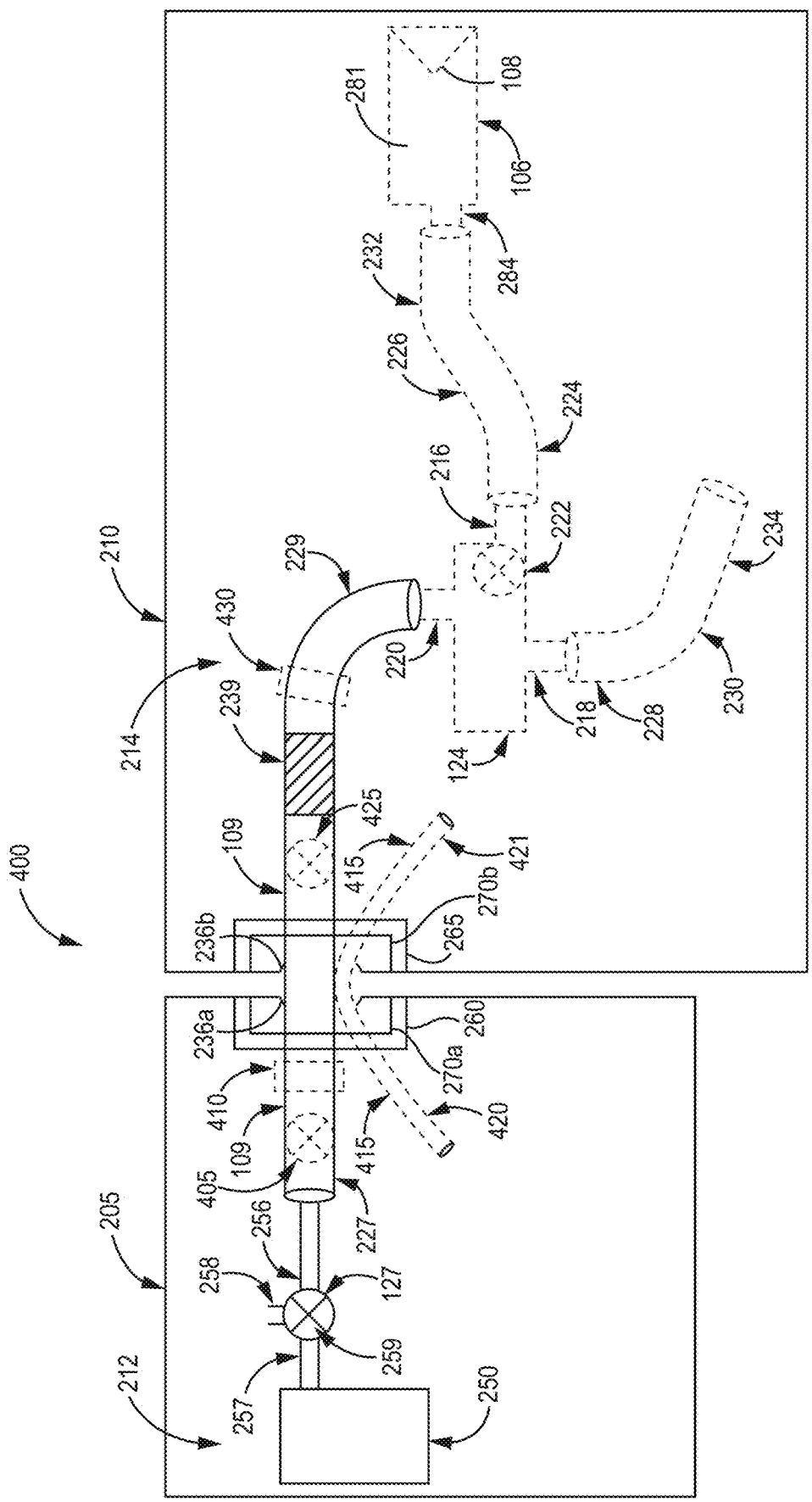
FIG. 6 is a schematic diagram showing a further embodiment of an injection setup kit including an exemplary first packaging container and an exemplary second packaging container.

FIG. 6 is a schematic diagram illustrating another embodiment of an injection setup kit 400. The injection setup kit 400 is similar to the injection setup kit 200 except that the components included in the first closed interior volume 212 of the first packaging container 205 and/or the second closed interior volume 214 of the second packaging container 210 may vary. Thus, reference characters shown in FIG. 6 for the injection setup kit 400 are used to convey the presence of like elements described previously with respect to the injection setup kit 200. Components shown in FIG. 6 in dashed lines are components that can optionally be included in the injection setup kit 400 depending on the particular application in which the injection setup kit 400 is to be used.

The components included within the first closed interior volume 212 of the first packaging container 205 in the injection setup kit 400 are the first fluid line end 227 of the fluid line 109, the patient interface connector 127, and the fluid collection receptacle 250. The patient interface connector 127 is fluidly connected to both the fluid collection receptacle 250 and the first fluid line end 227 within the first closed interior volume 212.

Depending on the application in which the injection setup kit 400 is to be used, the first closed interior volume 212 of the first packaging container 205 in the injection setup kit 400 can include one or more other components. For example, as shown in FIG. 6, one or more of (e.g., each of) a valve 405, a pressure measurement device 410, and a first fluid line end 420 of a fluid line 415 can be included within the first closed interior volume 212 of the first packaging container 205 in the injection setup kit 400. In one embodiment, the valve 405 can be a check valve that permits fluid flow toward the fluid collection receptacle 250 but restricts (e.g., prevents) fluid flow toward the second fluid line end 229. As shown here, the valve 405 can be located at the fluid line 109, though in other embodiments the valve 405 can be located at another component within the first closed interior volume 212. In one embodiment, the pressure measurement device 410 can be a pressure transducer configured to measure fluid pressure at the fluid line 109 and can be, for example, coupled to the first fluid line 109. And, in one embodiment, the first fluid line end 420 of a fluid line 415 can be included within the first closed interior volume 212. This first fluid line end 420 may be coupled to a component within the first closed interior volume 212 depending on the application. As shown here, the fluid line 415 can extend into the first closed interior volume 212 via the aperture 236a that the fluid line 109 extends into the first closed interior volume 212. Though in another embodiment a second aperture can be included at the first packaging container 205 for the fluid line 415 to separately extend into the first closed interior volume 212.

The components included within the second closed interior volume 214 of the second packaging container 210 in the injection setup kit 400 are the second fluid line end 229 of the fluid line 109 and the air detection interface 239.

Depending on the application in which the injection setup kit 400 is to be used, the second closed interior volume 214 of the second packaging container 210 in the injection setup kit 400 can include one or more other components. For example, as shown in FIG. 6, one or more of (e.g., each of) a valve 425, a pressure measurement device 430, the manifold connector 124, the fluid reservoir 106, and a second fluid line end 421 of the fluid line 415 can be included within the second closed interior volume 214 of the second packaging container 210 in the injection setup kit 400.

In one embodiment, the valve 425 can be a check valve that permits fluid flow toward the patient interface connector 127 but restricts (e.g., prevents) fluid flow toward the second fluid line end 229. As shown here, the valve 425 can be located at the fluid line 109, though in other embodiments the valve 425 can be located at another component within the second closed interior volume 214. In one example, only the valve 405 or the valve 425 may be included in the kit 400, but in another example both the valve 405 and the valve 425 may be included in the kit 400.

In one embodiment, the pressure measurement device 430 can be a pressure transducer configured to measure fluid pressure at the fluid line 109 and can be, for example, coupled to the first fluid line 109. In one example, only the pressure measurement device 410 or the pressure measurement device 430 may be included in the kit 400, but in another example both measurement devices 410 and 430 may be included in the kit 400.

In one embodiment, the manifold connector 124 and/or the fluid reservoir 106 can be included in the second closed interior volume 214. When the manifold connector 124 is included, the second fluid line end 229 of the fluid line 109 can be fluidly connected to the manifold connector 124 (e.g., at the manifold outlet 220) within the second closed interior volume 214. For instance, the second fluid line end 229 can include a Luer connector that is configured to fluidly connect to a complementary Luer connector at the manifold connector 124 (e.g., at the manifold outlet 220). When the fluid reservoir 106 is included in addition to the manifold connector 124, the reservoir 106 can be fluidly connected to the manifold connector 124 within the second closed interior volume 214 via the contrast fluid line 226 also included within the second closed interior volume 214.

And, in one embodiment, the second fluid line end 421 of the fluid line 415 can be included within the second closed interior volume 214. The second fluid line end 421 may be coupled to a component within the second closed interior volume 214 depending on the application. As shown here, the fluid line 415 can extend into the second closed interior volume 214 via the aperture 236*b* that the fluid line 109 extends into the second closed interior volume 214. Though in another embodiment a second aperture can be included at the second packaging container 210 for the fluid line 415 to separately extend into the second closed interior volume 214.

As described previously herein, when second packaging container 210 is opened, two or more of the components included within the second packaging container can be removed from the second closed interior volume 214 in a fluidly connected state. As one example, when these components are removed from the second closed interior volume 214, the manifold connector 124 can be in fluid communication with the patient interface connector 127 via the fluid line 109. As another example, the fluid reservoir 106 can be secured at the sleeve included at the drive assembly housing of a fluid injector. The fluid purge process can then be carried out in a manner as described with respect to the injection setup kit 200.

Embodiments of an exemplary application relating to a fluid injector have been described. However, a variety of other applications are within the scope of the present disclosure.

For example, other embodiments can include applications relating to other medical components. One medical component setup kit can include a first packaging container and a second packaging container. In this embodiment, the first packaging container can define a first closed interior volume that includes one or more first stage medical components and the second packaging container can define a second closed interior volume that includes one or more second stage medical components. This embodiment can also include a connection line having a first connection line end and a second connection line end. The first connection line end can be connected to one or more of the one or more first stage medical components within the first closed interior volume of the first packaging container. The second connection line end can extend outside of the first closed interior volume of the first packaging container. In one example, the second connection line end can be within the second closed interior volume of the second packaging container. For instance, in this example, the second connection line end can be connected one or more of the one or more second stage medical components within the second closed interior volume of the second packaging container. In this medical component setup kit embodiment, the first and second packaging containers can each define one or more apertures and/or include a face plate as described previously.

In the medical component setup kit embodiment, the one or more first stage medical components and the one or more second stage medical components can be components that are configured to be used in the same medical procedure. The one or more first stage medical components can be components configured to be set up in place and utilized at a first stage of the medical procedure, while the one or more second stage medical components can be components configured to remain in the second closed interior volume during the first stage of the medical procedure. For example, the first packaging container can be opened, and at least one of the one or more first stage medical components can be positioned appropriately outside of the interior volume of the first packaging container, while the second connection line end remains connected to one or more second stage medical components within the second closed interior volume. Then, an action relating to the medical procedure, such as a pre-procedure initialization action or a first step in the medical procedure, can be performed. After this action relating to the medical procedure is performed, the second packaging container can then be opened and at least one of the one or more second stage medical components can be positioned appropriately outside of the interior volume of the second packaging container. Then, another action relating to the medical procedure, such as a first step, second step, or any subsequent step, can be performed, for instance utilizing at least one of the one or more second stage medical components.

In one particular example, a medical component setup kit embodiment as described above can include a Fractional Flow Reserve (FFR) component setup kit. In one exemplary FFR component setup kit, the first closed interior volume of the first packaging container can include one or more of a first end of a guide wire, a first end of a signal line, and a proximal portion of a sensor delivery device. This exemplary FFR component setup kit can also include the second closed interior volume of the second packaging container having one or more of a second end of the guide wire, a second end of the signal line, and a distal portion of a sensor delivery device having a pressure sensor. The guide wire, the signal line, and the sensor delivery device (e.g., if each is included in a particular embodiment) can extend from the first interior volume into the second interior volume. This exemplary FFR component setup kit can allow the first packaging container to be opened so that one or more of the first end of the guide wire, the first end of the signal line, and the proximal portion of a sensor delivery device can be prepared for a FFR procedure, for instance by appropriately configuring these components with respect to a control console. Once these one or more components have been removed and prepared, the second packaging container can be opened so that one or more of the second end of the guide wire, the second end of the signal line, and the distal portion of a sensor delivery device having the pressure sensor can be inserted into a patient during the FFR procedure.

Figure 7:
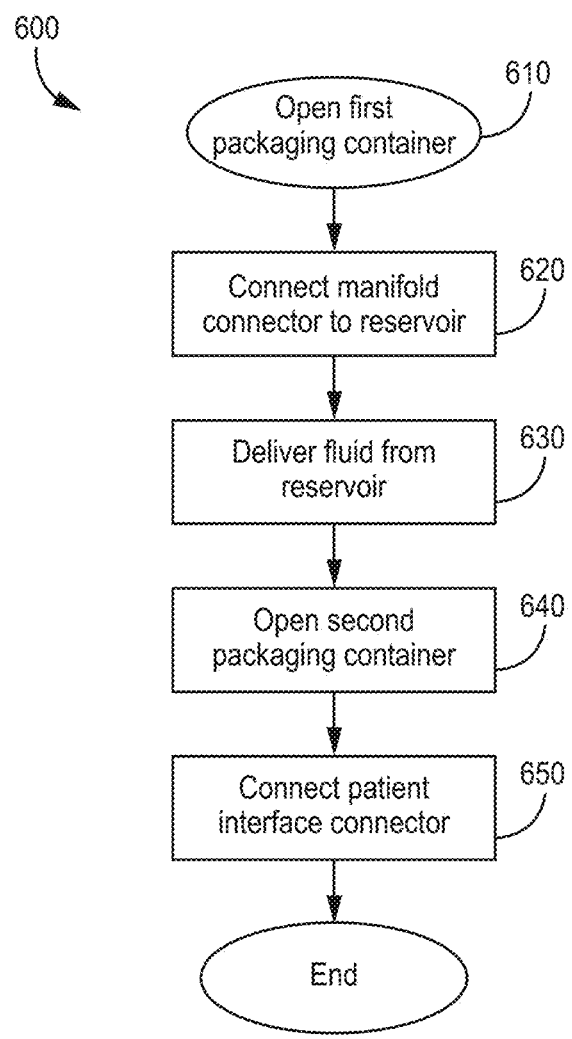
FIG. 7 is a flow diagram of an embodiment of a method of setting up an injection system.

FIG. 7 shows a flow diagram of an embodiment of a method 600 of setting up an injection system.

At step 610, a first packaging container is opened. As one example, the first packaging container referred to in this method 600 can be the same as, or similar to, the second packaging container 210 described elsewhere herein. In opening the first packaging container, step 610 can include removing from the first packaging container a manifold connector. The manifold connector removed from the first packaging container can include a first manifold inlet, a second manifold inlet, and a manifold outlet. The manifold outlet of the manifold connector removed from the first packaging container can be connected to one end of a fluid line. Another end of this fluid line can extend within a closed interior volume of a second packaging container. In some embodiments, the second packaging container can enclose the closed interior volume, and the second packaging container can include an aperture through which the another end of the fluid line extends into the closed interior volume. In many instances, opening the first packaging container at step 610 can include maintaining a sterile environment within the second packaging container. As one example, the second packaging container referred to in this method 600 can be the same as, or similar to, the first packaging container 205 described elsewhere herein.

In a further embodiment, opening the first packaging container at step 610 can also include removing from the first packaging container a flushing fluid line having a first flushing fluid line end and a second flushing fluid line end. The first flushing fluid line end can be connected to the second manifold inlet. In this further embodiment, after opening the first packaging container, the second flushing fluid line end can be connected to a flushing fluid reservoir. After connecting the second flushing fluid line end to the flushing fluid reservoir, flushing fluid can be delivered along the flushing fluid line to the fluid collection receptacle that is within the closed interior volume of the second packaging container.

At step 620, after opening the first packaging container, the first manifold inlet can be fluidly connected to a contrast fluid reservoir. The contrast fluid reservoir can define an internal reservoir volume that includes a first plunger.

At step 630, after connecting the first manifold inlet to the contrast fluid reservoir, contrast fluid can be delivered from the contrast fluid reservoir along the fluid line to a fluid collection receptacle that is within the closed interior volume of the second packaging container.

At step 640, after delivering contrast fluid to the fluid collection receptacle, the second packaging container can be opened. In opening the second packaging container, step 640 can include removing from the second packaging container the another end of the fluid line, the fluid collection receptacle, and a patient interface connector that is in fluid communication with the fluid line. The patient interface connector removed from the second packaging container can includes a patient interface inlet, a patient interface outlet, and a valve that is configured to selectively permit fluid to be communicated through the patient interface connector from the patient interface inlet to the patient interface outlet. For instance, the patient interface outlet of the patient interface connector can be fluidly connected to the fluid collection receptacle within the closed interior volume of the second packaging container prior to opening the second packaging container.

At step 650, after opening the second packaging container, the patient interface connector can be fluidly connected to an injection catheter. One or more fluids can be delivered from the connected fluid reservoir to the injection catheter. For example, after fluidly connecting the patient interface connector to the injection catheter, contrast fluid can be delivered from the contrast fluid reservoir along the fluid line to the injection catheter.

Various non-limiting exemplary embodiments have been described. It will be appreciated that suitable alternatives are possible without departing from the scope of the examples described herein. These and other examples are within the scope of the following claims.

What is claimed is:

1. An injection setup kit comprising:
   a first packaging container defining a first closed sterile interior volume that comprises:
      a patient interface connector including a patient interface inlet, a patient interface outlet, and a valve that is configured to selectively permit fluid to be communicated through the patient interface connector from the patient interface inlet to the patient interface outlet; and
      a fluid collection receptacle fluidly connected to the patient interface outlet;
   a second packaging container separate from the first packaging container, the second packaging container defining a second closed sterile interior volume that comprises a manifold connector including a manifold inlet and a manifold outlet; and
   a fluid line having a first fluid line end and a second fluid line end, wherein the first fluid line end is fluidly connected to the patient interface inlet within the first closed sterile interior volume of the first packaging container, and the second fluid line end is fluidly connected to the manifold outlet within the second closed sterile interior volume of the second packaging container;
   wherein:
      the first and second packaging containers comprise respective apertures through which the fluid line passes;
      the second packaging container is independently openable with respect to the first packaging containers such that when the second packaging container is opened, the first packaging container maintains its first closed sterile interior volume; and
      the fluid collection receptacle is configured to hold fluid output from the manifold outlet during an air purge process that is performed when the second packaging container is opened and the first packaging container maintains its first closed sterile interior volume.

2. The kit of claim 1, further comprising:
   a flushing fluid line having a first flushing fluid line end and a second flushing fluid line end, and
   wherein the manifold connector further includes a second manifold inlet, wherein the first flushing fluid line end is connected to the second manifold inlet within the second closed sterile interior volume of the second packaging container.

3. The kit of claim 1, wherein the second closed sterile interior volume of the second packaging container further comprises:
   an air detection interface downstream of the manifold outlet, the air detection interface configured to facilitate detection of the presence of air in the fluid line.

4. The kit of claim 1, wherein the second closed sterile interior volume of the second packaging container further comprises:
   a first fluid reservoir defining a first internal reservoir volume, the first internal reservoir volume including a first plunger.

5. The kit of claim 4, wherein the second closed sterile interior volume of the second packaging container further comprises:
   a contrast fluid line having a first contrast fluid line end and a second contrast fluid line end, the first contrast fluid line end connected to the first manifold inlet within the second closed sterile interior volume of the second packaging container and the second contrast fluid line end connected to the first fluid reservoir within the second closed sterile interior volume of the second packaging container.

6. The kit of claim 5, wherein the second closed sterile interior volume of the second packaging container further comprises:
a second fluid reservoir defining a second internal reservoir volume, the second internal reservoir volume including a second plunger.

7. The kit of claim 6, wherein the second closed sterile interior volume of the second packaging container further comprises:
a flushing fluid line having a first flushing fluid line end and a second flushing fluid line end,
wherein the manifold connector further includes a second manifold inlet, wherein the first flushing fluid line end is connected to the second manifold inlet within the second closed sterile interior volume of the second packaging container and the second flushing fluid line end is connected to the second fluid reservoir within the second closed sterile interior volume of the second packaging container.

8. The kit of claim 1, wherein the patient interface connector further includes a second patient interface outlet, and wherein the valve is configured to selectively permit fluid to be communicated through the patient interface connector from the patient interface inlet to either of the patient interface outlet and the second patient interface outlet.

9. The kit of claim 1, wherein the manifold connector includes a second manifold inlet and a manifold valve, and wherein the manifold valve is configured to move, in response to a change in pressure at the manifold connector, between a first manifold valve position in which the manifold valve blocks fluid communication from the first manifold inlet to the manifold outlet and a second manifold valve position in which the manifold valve blocks fluid communication from the second manifold inlet to the manifold outlet.

10. A method of setting up an injection system, the method comprising the steps of:
providing a first packaging container, a second packaging container, and a fluid line, wherein:
the first packaging container defining a first closed sterile interior volume that comprises:
a patient interface connector including a patient interface inlet, a patient interface outlet, and a valve that is configured to selectively permit fluid to be communicated through the patient interface connector from the patient interface inlet to the patient interface outlet; and
a fluid collection receptacle fluidly connected to the patient interface outlet;
the second packaging defines a second closed sterile interior volume that comprises a manifold connector including a manifold inlet and a manifold outlet; and
the fluid line has a first fluid line end and a second fluid line end, wherein the first fluid line end is fluidly connected to the patient interface inlet within the first closed sterile interior volume of the first packaging container, and the second fluid line end is fluidly connected to the manifold outlet within the second closed sterile interior volume of the second packaging container;
further wherein:
the first and second packaging containers comprise respective apertures through which the fluid line passes;
the second packaging container is independently openable with respect to the first packaging containers such that when the second packaging container is opened, the first packaging container maintains its first closed sterile interior volume; and
the fluid collection receptacle is configured to hold fluid output from the manifold outlet during an air purge process that is performed when the second packaging container is opened and the first packaging container maintains its first closed sterile interior volume
opening the second packaging container and removing from the second packaging container the manifold connector;
after opening the second packaging container, fluidly connecting the first manifold inlet to a contrast fluid source;
after connecting the manifold inlet to the contrast fluid source, delivering contrast fluid from the contrast fluid source along the fluid line to the fluid collection receptacle that is within the closed sterile interior volume of the first packaging container;
after delivering contrast fluid to the fluid collection receptacle, opening the first packaging container and removing from the first packaging container the another end of the fluid line, the fluid collection receptacle, and the patient interface connector; and
after opening the second packaging container, fluidly connecting the patient interface connector to an injection catheter.

11. The method of claim 10, wherein the manifold connector further includes a second manifold inlet, and wherein opening the second packaging container further comprises removing from the second packaging container a flushing fluid line having a first flushing fluid line end and a second flushing fluid line end, the first flushing fluid line end connected to the second manifold inlet.

12. The method of claim 11, further comprising the steps of:
after opening the second packaging container, connecting the second flushing fluid line end to a flushing fluid reservoir;
after connecting the second flushing fluid line end to the flushing fluid reservoir, delivering flushing fluid along the flushing fluid line to the fluid collection receptacle that is within the closed sterile interior volume of the first packaging container; and
after fluidly connecting the patient interface connector to the injection catheter, delivering contrast fluid from the contrast fluid source along the fluid line to the injection catheter.

* * * * *

UNITED STATES PATENT AND TRADEMARK OFFICE
CERTIFICATE OF CORRECTION

| | | |
|---|---|---|
| PATENT NO. | : 11,911,587 B2 | Page 1 of 1 |
| APPLICATION NO. | : 17/006973 | |
| DATED | : February 27, 2024 | |
| INVENTOR(S) | : Matthew James Russell Bakken et al. | |

It is certified that error appears in the above-identified patent and that said Letters Patent is hereby corrected as shown below:

In the Claims

In Column 22, Claim 5, Line 67, delete "first".

In Column 23, Claim 9, Line 37, delete "first".

In Column 24, Claim 10, Line 25, delete "first".

Signed and Sealed this
Eleventh Day of June, 2024

Katherine Kelly Vidal
*Director of the United States Patent and Trademark Office*